United States Patent
Liran (12) 
(10) Patent No.: US 10,121,533 B2
(45) Date of Patent: Nov. 6, 2018

(54) TECHNIQUES FOR DATA RETENTION IN MEMORY CELLS DURING POWER INTERRUPTION

(71) Applicant: NANO-RETINA, INC., Wilmington, DE (US)

(72) Inventor: Tuvia Liran, Qiryat Tivon (IL)

(73) Assignee: NANO-RETINA, INC., Wilmington, DE (US)

( * ) Notice: Subject to any disclaimer, the term of this patent is extended or adjusted under 35 U.S.C. 154(b) by 251 days.

(21) Appl. No.: 14/965,362

(22) Filed: Dec. 10, 2015

(65) Prior Publication Data

US 2016/0099046 A1    Apr. 7, 2016

Related U.S. Application Data

(63) Continuation-in-part of application No. 13/683,158, filed on Nov. 21, 2012, now Pat. No. 9,720,477.

(51) Int. Cl.
*G11C 11/417* (2006.01)
*G11C 5/14* (2006.01)
(Continued)

(52) U.S. Cl.
CPC ............ *G11C 11/417* (2013.01); *G11C 5/143* (2013.01); *H01L 27/1104* (2013.01); *A61F 2/14* (2013.01);
(Continued)

(58) Field of Classification Search
CPC ... G11C 11/417; G11C 5/143; H01L 27/1104; A61F 2/14
See application file for complete search history.

(56) References Cited

U.S. PATENT DOCUMENTS 4,197,850 A    4/1980  Schulman et al.
4,262,294 A    4/1981  Hara et al.
(Continued)

FOREIGN PATENT DOCUMENTS

CA    2235216    4/1997
CN    1875895    12/2006
(Continued)

OTHER PUBLICATIONS

An International Search Report and a Written Opinion both dated Feb. 21, 2017, which issued during the prosecution of Applicant's PCT/US2016/065784.
(Continued)

*Primary Examiner* — Terrell S Johnson
(74) *Attorney, Agent, or Firm* — Sughrue Mion, PLLC (57) ABSTRACT

Volatile memory is described, comprising: (i) a first inverter comprising a first p-type field effect transistor (FET) connected to a first n-type FET; (ii) a second inverter comprising a second p-type FET connected to a second n-type FET; (iii) a third p-type FET; (iv) a fourth p-type FET; and (v) a floating line connecting (i) a source of the third p-type FET, and (ii) a source of the fourth p-type FET, wherein: (a) the first data line is connected to: a gate of the second p-type FET, a gate of the second n-type FET, a drain of the third p-type FET, and a gate of the fourth p-type FET, and (b) the second data line is connected to: a gate of the first p-type FET, a gate of the first n-type FET, a drain of the fourth p-type FET, and a gate of the third p-type FET.

27 Claims, 7 Drawing Sheets

(51) Int. Cl.
  *H01L 27/11* (2006.01)
  *A61N 1/36* (2006.01)
  *A61N 1/378* (2006.01)
  *A61F 2/14* (2006.01)
(52) U.S. Cl.
  CPC ........ *A61N 1/36046* (2013.01); *A61N 1/3787* (2013.01)

(56) References Cited

U.S. PATENT DOCUMENTS

| | | | |
|---|---|---|---|
| 4,324,252 A | 4/1982 | Rossing et al. | |
| 4,595,999 A | 6/1986 | Betirac | |
| 4,628,933 A | 12/1986 | Michelson | |
| 4,825,350 A | 4/1989 | Brackman | |
| 4,827,261 A | 5/1989 | Trofimenkoff et al. | |
| 5,313,642 A | 5/1994 | Seigel | |
| 5,314,458 A | 5/1994 | Najafi et al. | |
| 5,324,961 A * | 6/1994 | Rodder | G11C 11/4125 257/306 |
| 5,712,795 A | 1/1998 | Layman et al. | |
| 5,735,882 A | 4/1998 | Rottenberg et al. | |
| 5,769,875 A | 6/1998 | Peckham | |
| 5,850,514 A | 12/1998 | Gonda et al. | |
| 6,035,236 A | 3/2000 | Jarding et al. | |
| 6,331,947 B1 * | 12/2001 | Widdershoven | G11C 7/20 365/104 |
| 6,888,571 B1 | 5/2005 | Koshizuka et al. | |
| 6,976,998 B2 | 12/2005 | Rizzo et al. | |
| 7,006,873 B2 | 2/2006 | Chow et al. | |
| 7,047,080 B2 | 5/2006 | Palanker | |
| 7,248,928 B2 | 7/2007 | Yagi | |
| 7,302,598 B2 | 11/2007 | Suzuki | |
| 7,342,427 B1 | 3/2008 | Fensore | |
| 7,831,309 B1 | 11/2010 | Humayun et al. | |
| 8,000,804 B1 | 8/2011 | Wessendorf et al. | |
| 8,150,526 B2 | 4/2012 | Gross | |
| 8,428,740 B2 | 4/2013 | Gefen | |
| 8,442,641 B2 | 5/2013 | Gross | |
| 8,953,365 B2 | 2/2015 | Erickson et al. | |
| 2001/0011844 A1 | 8/2001 | Ernst et al. | |
| 2002/0024049 A1 * | 2/2002 | Nii | G11C 8/16 257/67 |
| 2002/0136034 A1 | 9/2002 | Feldtkeller | |
| 2003/0181957 A1 | 9/2003 | Grennberg et al. | |
| 2004/0054407 A1 | 3/2004 | Tashiro et al. | |
| 2004/0082981 A1 | 4/2004 | Chow et al. | |
| 2004/0088026 A1 | 5/2004 | Chow et al. | |
| 2004/0098067 A1 | 5/2004 | Ohta et al. | |
| 2004/0103343 A1 | 5/2004 | Wu et al. | |
| 2005/0015120 A1 | 1/2005 | Seibel et al. | |
| 2005/0146954 A1 | 7/2005 | Win | |
| 2005/0168569 A1 | 8/2005 | Igarashi et al. | |
| 2006/0106432 A1 | 5/2006 | Coulombe | |
| 2006/0256989 A1 | 11/2006 | Olsen et al. | |
| 2006/0287688 A1 | 12/2006 | Yonezawa | |
| 2007/0222411 A1 | 9/2007 | Cour | |
| 2008/0164762 A1 | 7/2008 | Pecile | |
| 2008/0288067 A1 | 11/2008 | Flood | |
| 2008/0294224 A1 | 11/2008 | Grennberg et al. | |
| 2009/0002034 A1 | 1/2009 | Hoefnagel | |
| 2009/0216295 A1 | 8/2009 | Zrenner et al. | |
| 2009/0228069 A1 | 9/2009 | Dai | |
| 2010/0087895 A1 | 4/2010 | Zhou et al. | |
| 2010/0204754 A1 | 8/2010 | Gross et al. | |
| 2010/0249878 A1 | 9/2010 | McMahon | |
| 2010/0331682 A1 | 12/2010 | Stein | |
| 2011/0054583 A1 | 3/2011 | Litt | |
| 2011/0172736 A1 | 7/2011 | Gefen | |
| 2011/0254661 A1 | 10/2011 | Fawcett et al. | |
| 2012/0035725 A1 | 2/2012 | Gefen | |
| 2012/0035726 A1 | 2/2012 | Gross et al. | |
| 2012/0041514 A1 | 2/2012 | Gross | |
| 2012/0194781 A1 | 8/2012 | Agurok | |
| 2012/0221103 A1 | 8/2012 | Liran | |
| 2012/0259410 A1 | 10/2012 | Gefen | |
| 2012/0268080 A1 | 10/2012 | Jeon et al. | |
| 2012/0283800 A1 | 11/2012 | Perryman et al. | |
| 2013/0006326 A1 | 1/2013 | Ackermann et al. | |
| 2013/0126713 A1 | 5/2013 | Haas et al. | |
| 2013/0322462 A1 | 12/2013 | Poulsen | |
| 2014/0031931 A1 | 1/2014 | Liran et al. | |
| 2014/0047713 A1 | 2/2014 | Singh et al. | |
| 2014/0143559 A1 | 5/2014 | Gefen et al. | |
| 2014/0146132 A1 * | 5/2014 | Bagnato | G02B 27/2228 348/36 |

FOREIGN PATENT DOCUMENTS

| | | |
|---|---|---|
| DE | 10315397 | 10/2004 |
| JP | 2000350742 | 12/2000 |
| WO | 2001/074444 | 10/2001 |
| WO | 2007/076347 | 7/2007 |
| WO | 2010/089739 | 8/2010 |
| WO | 2011/086545 | 7/2011 |
| WO | 2011/163262 | 12/2011 |
| WO | 2012/017426 | 2/2012 |
| WO | 2012/114327 | 8/2012 |
| WO | 2012/153325 | 11/2012 |

OTHER PUBLICATIONS

European Search Report dated Feb. 9, 2017, which issued during the prosecution of Applicant's European App No. 12748896.3.
An Office Action dated Aug. 20, 2015, which issued during the prosecution of U.S. Appl. No. 14/160,314.
An International Search Report and a Written Opinion both dated Jun. 30, 2015, which issued during the prosecution of Applicant's PCT/IB2014/067417.
An International Search Report and a Written Opinion both dated Jun. 30, 2015, which issued during the prosecution of Applicant's PCT/IB2015/050224.
An Invitation to pay additional fees dated Mar. 24, 2015, which issued during the prosecution of Applicant's PCT/IB2014/067417.
An Invitation to pay additional fees dated Mar. 31, 2015, which issued during the prosecution of Applicant's PCT/IB2015/050224.
An Office Action dated Feb. 5, 2015, which issued during the prosecution of U.S. Appl. No. 14/199,462.
An Office Action dated Nov. 27, 2013 which issued during the prosecution of Japanese Patent Application No. 2011-548843.
European Search Report dated Apr. 16, 2014, which issued during the prosecution of Applicant's European App No. 11732733.8.
An Office Action dated Mar. 3, 2015, which issued during the prosecution of U.S. Appl. No. 13/148,461.
Interview Summary Report dated Apr. 23, 2015, which issued during the prosecution of U.S. Appl. No. 13/683,158.
An Office Action dated Feb. 3, 2015, which issued during the prosecution of U.S. Appl. No. 13/683,158.
An Office Action dated Nov. 19, 2015, which issued during the prosecution of U.S. Appl. No. 13/683,158.
European Search Report dated Feb. 20, 2015, which issued during the prosecution of Applicant's European App No. 12782462.1.
An Office Action dated Apr. 14, 2015, which issued during the prosecution of U.S. Appl. No. 14/018,850.
J.F. Rizzo, "Methods and Perceptual Thresholds for Short-Term Electrical Stimulation of Human Retina with Microelectrode Arrays", Investigative Ophthalmology and Visual Science, vol. 44, No. 12, (Dec. 1, 2003) pp. 5355-5361.
Merriam-Webster. Merriam-Webster, n.d. Web. Nov. 2, 2015. <http://www.merriam-webster.com/dictionary/periodically>.
An International Search Report and a Written Opinion both dated Feb. 27, 2014, which issued during the prosecution of Applicant's PCT/IB2013/060270.
European Search Report dated Nov. 19, 2013, which issued during the prosecution of Applicant's European App No. 11814197.7.
European Search Report dated Feb. 26, 2014, which issued during the prosecution of Applicant's European App No. 10738277.2.
Interview Summary Report dated Mar. 24, 2016, which issued during the prosecution of U.S. Appl. No. 13/683,158.

(56) References Cited

OTHER PUBLICATIONS

An Office Action dated Jul. 27, 2016, which issued during the prosecution of U.S. Appl. No. 13/683,158.

* cited by examiner

TECHNIQUES FOR DATA RETENTION IN MEMORY CELLS DURING POWER INTERRUPTION

CROSS-REFERENCES TO RELATED APPLICATIONS

The present application is a Continuation-in-Part of US 13/683158 to Gefen et al., filed Nov. 21, 2012, and entitled "Weak Power Supply Operation and Control," which published as US 2014/0143559 (now U.S. Pat.No. 9,720,477), and which is incorporated herein by reference.

FIELD OF THE INVENTION

Some applications of the present invention relate in general to volatile memory in semiconductor micro-chips. More specifically, some applications of the present invention relate to retaining data in volatile memory during power interruption.

BACKGROUND

Volatile memory, such as Random Access Memory (RAM), requires supply voltage to retain data stored within; it retains its contents while powered but when power is interrupted the stored data might be lost rapidly. Using non-volatile memory is an option for retaining the data during power interruption, but implementing such memory requires special processes and circuits, or requires high voltage for programming, which requires a significant increase of complexity and cost.

SUMMARY OF THE INVENTION

For some applications of the invention, each memory circuit (e.g., memory element) of a volatile memory device is provided with its own charge reserve, comprising a pair of transistors, with an electrical connection between them. Capacitance at the electrical connection is charged by normal functioning of the memory circuit, and provides power to the memory circuit during interruption of the device's main power supply, thereby retaining the data stored in the memory circuit as long as there is sufficient charge in the reserve. For some applications this capacitance is provided by an electrical capacitive element, such as a distinct capacitor. For some applications, this capacitance is provided by inherent capacitance (e.g., parasitic capacitance) at the electrical connection.

For some applications the electrical connection also connects the transistor pair of one memory circuit to the transistor pair of one or more other memory circuits. That is, for some applications, a common charge reserve is shared by more than one memory circuit.

Typically, each memory circuit comprises a pair of cross-coupled inverters (e.g., CMOS inverters), and the transistor pair of the charge reserve is electrically connected between the inverters.

There is therefore provided, in accordance with an application of the present invention, apparatus including a volatile memory, the volatile memory having a first data line and a second data line, and including:

a first inverter including a first p-type field effect transistor (FET) connected to a first n-type FET;

a second inverter including a second p-type FET connected to a second n-type FET, and cross-coupled with the first inverter;

a third p-type FET;

a fourth p-type FET; and a floating line connecting (i) a source of the third p-type FET, and (ii) a source of the fourth p-type FET, and:

the first data line is connected to:
a gate of the second p-type FET,
a gate of the second n-type FET,
a drain of the third p-type FET, and
a gate of the fourth p-type FET, and
the second data line is connected to:
a gate of the first p-type FET,
a gate of the first n-type FET,
a drain of the fourth p-type FET, and
a gate of the third p-type FET.

In an application, the apparatus further includes a capacitor that includes a first plate and a second plate, and the floating line connects (i) the source of the third p-type FET, (ii) the source of the fourth p-type FET, and (iii) the first plate of the capacitor.

In an application, (i) the second plate of the capacitor, (ii) a drain of the first n-type FET, and (iii) a drain of the second n-type FET are connected to ground.

In an application, the floating line is further connected to (i) an n-well of the first p-type FET, and (ii) an n-well of the second p-type FET.

There is further provided, in accordance with an application of the present invention, apparatus including a volatile memory device including one or more memory circuits, each memory circuit including:

a first CMOS inverter, having a first input and a first output;

a second CMOS inverter, cross-coupled to the first CMOS inverter, and having a second input and a second output;

a first PMOS transistor, having a first source, a first gate, and a first drain;

a second PMOS transistor, having a second source electrically connected to the first source, a second gate, and a second drain;

a first connector, electrically connecting:
the first output,
the first drain,
the second gate, and
the second input; and
a second connector, electrically connecting:
the second output,
the second drain,
the first gate, and
the first input.

In an application:
the first CMOS inverter includes a third PMOS transistor having a third source, a third gate, a third drain, and a third-transistor n-well,
the second CMOS inverter includes a fourth PMOS transistor having a fourth source, a fourth gate, a fourth drain, and a fourth-transistor n-well, and
each memory circuit further includes a third connector, electrically connecting the first source, the second source, the third-transistor n-well, and the fourth-transistor n-well.

In an application, each memory circuit is an SRAM cell.

In an application, each memory circuit is a latch.

In an application, each memory circuit is a six-transistor SRAM cell.

In an application, each memory circuit is an eight-transistor SRAM cell.

In an application, each memory circuit is a ten-transistor SRAM cell.

In an application:

the first PMOS transistor has a first-transistor threshold voltage, the first CMOS inverter includes a third PMOS transistor having a third-transistor threshold voltage, and the first PMOS transistor is configured such that the first-transistor threshold voltage is greater than the third-transistor threshold voltage.

In an application, the first PMOS transistor is configured such that the first-transistor threshold voltage is greater than the third-transistor threshold voltage by between 0.05 and 0.2 V.

In an application, each memory circuit further includes a third connector, electrically connecting the first source and the second source, and each memory circuit further includes an electrical capacitive element that includes a first conductor and a second conductor, and the third connector electrically connects the first source, the second source, and the first conductor.

In an application, the electrical capacitive element includes a distinct capacitor.

In an application, each memory circuit further includes a third connector, electrically connecting the first source and the second source, and the apparatus further includes a dielectric in electrical contact with the third connector.

In an application, the dielectric is a substrate on which the first, second, and third connectors are disposed.

In an application, the one or more memory circuits includes at least a first memory circuit and a second memory circuit, and the apparatus further includes a third connector, electrically connecting:
the first source of the first memory circuit,
the second source of the first memory circuit,
the first source of the second memory circuit, and
the second source of the second memory circuit.

In an application, the apparatus further includes an electrical capacitive element that includes a first conductor and a second conductor, and the third connector electrically connects:
the first conductor,
the first source of the first memory circuit,
the second source of the first memory circuit,
the first source of the second memory circuit, and
the second source of the second memory circuit.

In an application, the electrical capacitive element includes a distinct capacitor.

In an application, the apparatus further includes a dielectric in electrical contact with the third connector.

In an application, the dielectric is a substrate on which the first, second, and third connectors are disposed.

In an application, the apparatus includes a medical implant that includes the device.

In an application, the medical implant is an artificial retina implant.

In an application, the artificial retina implant is an optically-powered artificial retina implant.

In an application, the medical implant is a wirelessly-powered and battery-less medical implant.

There is further provided, in accordance with an application of the present invention, a Static Random Access Memory (SRAM) device, including one or more SRAM cells, each SRAM cell including:
a first CMOS inverter, having a first input and a first output;
a second CMOS inverter, cross-coupled to the first CMOS inverter, and having a second input and a second output;
a first PMOS transistor, having a first source, a first gate, and a first drain;

a second PMOS transistor, having a second source, a second gate, and a second drain;
an electrical capacitive element, including a first conductor and a second conductor;
a first connector, electrically connecting:
the first output,
the first drain,
the second gate, and
the second input;
a second connector, electrically connecting:
the second output,
the second drain,
the first gate, and
the first input; and
a third connector, electrically connecting:
the first source,
the second source, and
the first conductor.

There is further provided, in accordance with an application of the present invention, circuitry, including:
a volatile memory storing data and powered by a supply voltage; and
a capacitor connected to the volatile memory and configured, in response to a change in the supply voltage, to store the supply voltage and subsequently discharge the supply voltage at a preset rate so as to maintain the data stored in the volatile memory for a preset time.

In an application, the volatile memory includes a single bit memory, and the capacitor is charged from data lines of the single bit memory.

In an application, the discharge is to at least one of the data lines.

In an application, the supply voltage changes to a value less than 0.5 volts.

In an application, the supply voltage changes to a value less than 0.1 volts.

There is further provided, in accordance with an application of the present invention, a circuitry, including:
a volatile memory storing data and powered by a supply voltage; and
an energy storage device connected to the volatile memory and configured, in response to a change in the supply voltage, to store the supply voltage and subsequently discharge the supply voltage at a preset rate so as to maintain the data stored in the volatile memory for a preset time.

The present invention will be more fully understood from the following detailed description of applications thereof, taken together with the drawings, in which:

DETAILED DESCRIPTION OF EMBODIMENTS

Figure 1:
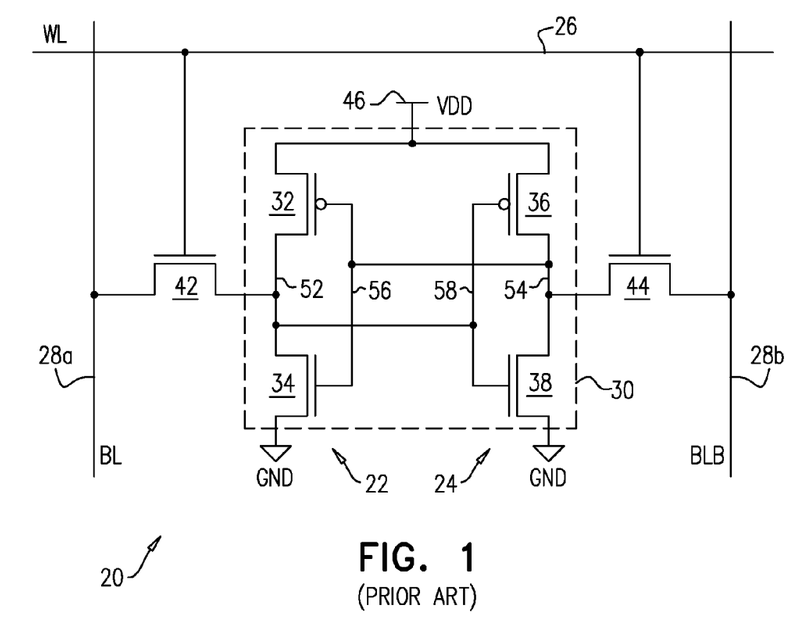
FIG. 1 is a schematic illustration of a prior art memory circuit, which is a conventional static random-access memory (SRAM) cell.

Reference is made to FIG. 1, which is a schematic illustration of a prior art memory circuit 20, which is a static random-access memory (SRAM) cell. Memory circuit 20 has six transistors: transistor 32, transistor 34, transistor 36, and transistor 38 are connected to form two cross-coupled inverters (e.g., complementary metal-oxide-semiconductor (CMOS) inverters) 22 and 24, each inverter having a positive-channel metal-oxide semiconductor (PMOS) transistor (32 and 36, respectively) and a negative-channel metal-oxide semiconductor (NMOS) transistor (34 and 38, respectively). Together, cross-coupled inverters 22 and 24, define a data-storage portion 30 of circuit 20. A power supply 46 provides power to memory circuit 20 in order for the memory circuit (e.g., data-storage portion 30 thereof) to maintain the data (i.e., the bit) stored therewithin.

Memory circuit 20 is accessed via word line 26. Memory circuit 20 further includes two access transistors 42 and 44, which are controlled by word line 26, and which themselves control the connection of memory circuit 20 (or portion 30 thereof) to one or more bit lines 28 (e.g., bit line 28a and bit line 28b) during read and write operations.

The structure and function of memory circuit 20 may be described using the following convention: Each of inverters 22 and 24 has (i) an input (52 and 54, respectively), between the drain of one of its transistors (32 and 36, respectively) and the source of its other transistor (34 and 38, respectively), and (ii) an output (56 and 58, respectively), between the respective gates of its transistors. Transistor 42 controls the connection of bit line 28a to input 52, and transistor 44 controls the connection of bit line 28b to input 54. The cross-coupling described hereinabove refers to the input of each of inverters 22 and 24 being electrically connected to the output of the other of the inverters. It will be understood by one skilled in the art that this cross-coupling means that as long as power supply 46 is maintained, (a) when input 52 is at voltage VDD of power supply 46, (i) output 58 is at voltage VDD, and (ii) output 56 and input 54 are at the voltage GND of ground, and (b) vice versa. This is the basis of data storage in a memory circuit comprising cross-coupled inverters. Throughout this patent application, the convention is used whereby a stored 1 corresponds to 52=VDD, 54=GND, 56=GND, 58=VDD; and a stored 0 corresponds to 52=GND, 54=VDD, 56=VDD, 58=GND.

Figure 2:
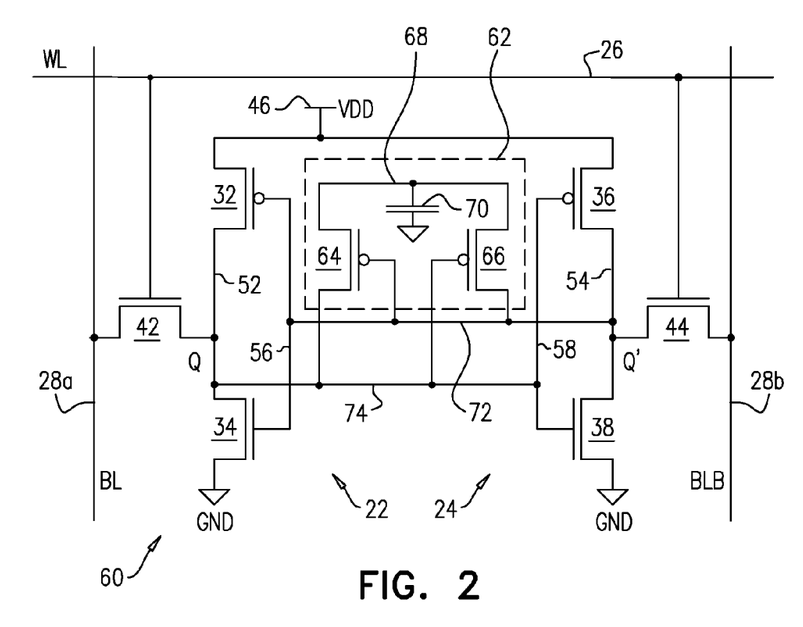
FIG. 2 is a schematic illustration of a memory circuit comprising a charge reserve, in accordance with some applications of the invention.

Reference is now made to FIG. 2, which is a schematic illustration of a memory circuit 60, comprising memory circuit 20 and a charge reserve 62, in accordance with some applications of the invention. Although reference numerals 20 and 30 are not used in FIG. 2, it is to be noted that the elements of memory circuit 20, including portion 30 (e.g., cross-coupled inverters 22 and 24), are present in memory circuit 60.

Connected between cross-coupled inverters 22 and 24 is a pair of transistors comprising a transistor 64 and a transistor 66, which are typically PMOS transistors. The source of transistor 64 is electrically connected to the source of transistor 66, e.g., by a connector 68. Transistors 64 and 66 are thereby connected between inverters 22 and 24 such that regardless of whether a 1 or a 0 is stored, one of transistors 64 and 66 will be acting as an open switch, and the other one will be acting as a closed switch. Therefore, while sufficient power is provided by power supply 46, connector 68 is maintained at generally the same voltage as supply 46, irrespective of whether a 1 or a 0 is stored.

Capacitance is provided at connector 68, e.g., by an electrical capacitive element (such as a discrete capacitor or a reverse-biased diode) 70 coupled to the connector, or by inherent capacitance (such as parasitic capacitance) of the connector (e.g., due to its interaction with surrounding materials, such as the substrate on which the connector is disposed, e.g., a dielectric). For some applications, capacitor 70 has a value of about 100-1000 femtofarads. For some applications, a battery is provided at connector 68. Therefore, while power is provided by power supply 46, this capacitance (e.g., capacitive element 70) will be charged and maintained, irrespective of whether a 1 or a 0 is stored (i.e., via either transistor 64 or via transistor 66). For example, if a 1 is stored, PMOS transistor 64 is closed due to input 54 and output 56 (which are electrically connected to the gate of transistor 64) being at voltage GND, and the capacitance is charged via transistor 64. Conversely, if a 0 is stored, PMOS transistor 66 is closed due to input 52 and output 58 (which are electrically connected to the gate of transistor 66) being at voltage GND, and the capacitance is charged via transistor 66. Therefore, this capacitance is charged by the normal data-storage functionality of memory circuit 60.

Reference is now made to FIGS. 1 and 2. In prior art memory circuit 20, in the event that power supply 46 is interrupted, the voltage at inverters 22 and 24 will drop rapidly, and the stored bit will be lost. For example, if a 1 is stored when power supply 46 is interrupted, the voltage at input 52 and output 58 will drop to GND. When power supply 46 is restored, memory circuit may therefore assume a random state, or may succumb to a default state; either way, the stored bit is lost.

In contrast, in memory circuit 60, as the voltage at inverters 22 and 24 begins to drop, the capacitance at connector 68 (e.g., electrical capacitive element 70) will begin to discharge through the source of whichever transistor 64 or 66 is currently closed, thereby slowing down the voltage drop, and retaining the stored bit for longer. For example, if circuit 60 stores a 1 (in which case, as described above, transistor 64 is closed), as the voltage at input 52 and output 58 begins to drop toward GND due to interruption in power supply 46, charge begins to flow from the capacitance at connector 68 (e.g., from capacitive element 70) through transistor 64, thereby slowing the rate at which the voltage at input 52 and output 58 drops. If power supply 46 is restored sufficiently soon (i.e., before the voltage at input 52 and output 58 drops below a minimum retaining voltage of circuit 60), the stored bit is not lost.

Therefore, memory circuit 60 may be described as comprising:

a first CMOS inverter 22, having a first input 52 and a first output 56;

a second CMOS inverter 24, cross-coupled to the first CMOS inverter, and having a second input 54 and a second output 58;

a first PMOS transistor 66, having a first source, a first gate, and a first drain;

a second PMOS transistor 64, having a second source electrically connected to the first source, a second gate, and a second drain;

a first connector 72, electrically connecting:
first output 56,
the drain of first transistor 66,
the gate of second transistor 64, and
second input 54; and a second connector 74, electrically connecting:
second output 58,
the drain of second transistor 64,
the gate of first transistor 66, and
first input 52.

Memory circuit 60 may be described as a six-transistor (6T) SRAM cell that further comprises charge reserve 62.

For some applications, transistors 64 and 66 have a higher threshold voltage than do transistors 32 and 36. That is, the PMOS transistors of charge reserve 62 may have a higher threshold voltage than do the transistors of data-storage portion 30 (i.e., of inverters 22 and 24 thereof). It is hypothesized by the inventors that this higher threshold slows the discharge of the capacitance at connector 68 (e.g., the discharge of electrical capacitive element 70). For example, transistors 64 and 66 may have a threshold voltage that is greater than the threshold voltage of transistors 32 and 36 by no more than 0.2 V (e.g., by 0.05-0.2 V).

For some applications, circuit 60 may be alternatively or additionally described as follows:

Memory circuit 60 is a modified version of a standard SRAM (static random access memory) cell. Typically a plurality of memory circuits generally similar to circuit 60 are formed into a memory module.

Memory circuit 60 comprises a p-type and an n-type field effect transistor (FET), 32 and 34, which are connected to form a first inverter 22. The gates of transistors 32 and 34 are connected to each other and to a data line Q'. The source of transistor 34 is connected to the drain of transistor 32 and to a data line Q, the source of transistor 32 is connected to power rail VDD, and the drain of transistor 34 is connected to ground rail GND.

Memory circuit 60 also comprises a p-type FET 36 and an n-type FET 38 which are connected to form a second inverter 24. The gates of transistors 36 and 38 are connected to each other and to the Q line. The source of 38 is connected to the drain of transistor 36 and to the Q' line, the source of transistor 36 is connected to power rail VDD, and the drain of transistor 38 is connected to ground rail GND.

Two n-type FETs, 42 and 44, are respectively connected to the Q and Q' data lines. A WL line is connected to gates of transistors 42 and 44, and enables the values of Q and Q' to be read from and written to via respective lines BL and BLB.

A p-type FET 64 has its drain connected to the Q line, and its source connected via a floating line 68 to a first plate of a capacitor 70. A second plate of the capacitor is connected to ground. The gate of transistor 64 is connected to the Q' line. As explained below, capacitor 70 acts as an electrical energy storage device, supplying the voltage required to memory circuit 60 for a limited period of time (e.g., for applications in which circuit 60 is part of an externally-powered intraocular implant and has brief power interruptions during eye blinks and saccades, as described herein-below with reference to FIG. 10, capacitor 70 may have a capacitance of about 100-1000 femtofarads, and the limited period of time is up to 30, 200 or 1000 ms). However, capacitor 70 is only one possible example of a suitable electrical energy storage device for the memory circuit, and other suitable storage devices that are capable of supplying voltage and that may substitute for capacitor 70 will be apparent to those having ordinary skill in the art. Such other devices include, but are not limited to, chemical batteries or photovoltaic cells, and all such devices are assumed to be comprised within the scope of the present invention.

A p-type FET 66 has its drain connected to the Q' line, and its source connected via line 68 to the first plate of capacitor 70. The gate of transistor 66 is connected to the Q line.

While power supply 46 supplies its specified voltage VDD to memory circuit 60, transistors 32, 34, 36, 38, 64, and 66 act as a single bit memory, the values of lines Q and Q' taking the values of 1 or 0, depending on the values input on lines BL and BLB. In addition, one of transistors 64 or 66 conducts while the other does not conduct. The conduction maintains the first plate of capacitor 70 in a charged state.

If power supply 46 changes so that the voltage VDD supplied is low, typically below the threshold voltage of transistors 32 and 36 (and even if VDD is zero), then capacitor 70 begins to discharge through the transistor, 64 or 66, conducting at the time when the power supply is below the voltage in floating line 68. The out of specification situation typically occurs when VDD is a few tens or hundreds of millivolts. The discharge maintains the potential of the line Q or Q' that is receiving the charge from capacitor 70, until the capacitor has completely discharged.

Without the presence of capacitor 70 and FETs 64 and 66, data loss may be caused once VDD drops below a predetermined voltage, which is proportional to an offset voltage created by any mismatch between the first and second invertors. While the mismatch may be theoretically limited, in practice processing variations may generate an offset. Applying the combination of capacitor 70 with FETs 64 and 66 allows data to be maintained in memory cell 60 even when voltage VDD is extremely low or even zero, for a limited period of time (e.g., tens or hundreds of milliseconds).

The length of time for which the data may be maintained is dependent on the capacitance of capacitor 70, and on the resistance offered by FETs 64 and 66. Thus for a high capacitance and resistance the time over which the data may be maintained is of the order of tens or more milliseconds after a complete power down of VDD. Capacitor 70 may be implemented by any convenient method, such as by separating two polysilicon layers by a silicon dioxide dielectric (a poly-poly capacitor) or by separating two metal layers by a dielectric. Alternatively or additionally, capacitor 70 may be at least partially implemented using the gate of a transistor, by methods well known in the art.

The description above has assumed that capacitor 70 supplies charge to a single memory circuit, memory circuit 60. In alternative embodiments of the present invention a single capacitor is configured to supply charge to a plurality of memory circuits, substantially similar to memory circuit 60, each having eight transistors as illustrated in FIG. 2. In the alternative embodiments, line 68 is connected as a shared floating power supply line to the sources of the respective FETs 64, 66 in each of the plurality of memories, e.g., as described with reference to FIG. 3.

As described hereinabove, for some applications a distinct capacitor 70 is not provided, but rather inherent capacitance (e.g., parasitic capacitance) is used. An example of this is described with reference to FIG. 7.

Figure 3:
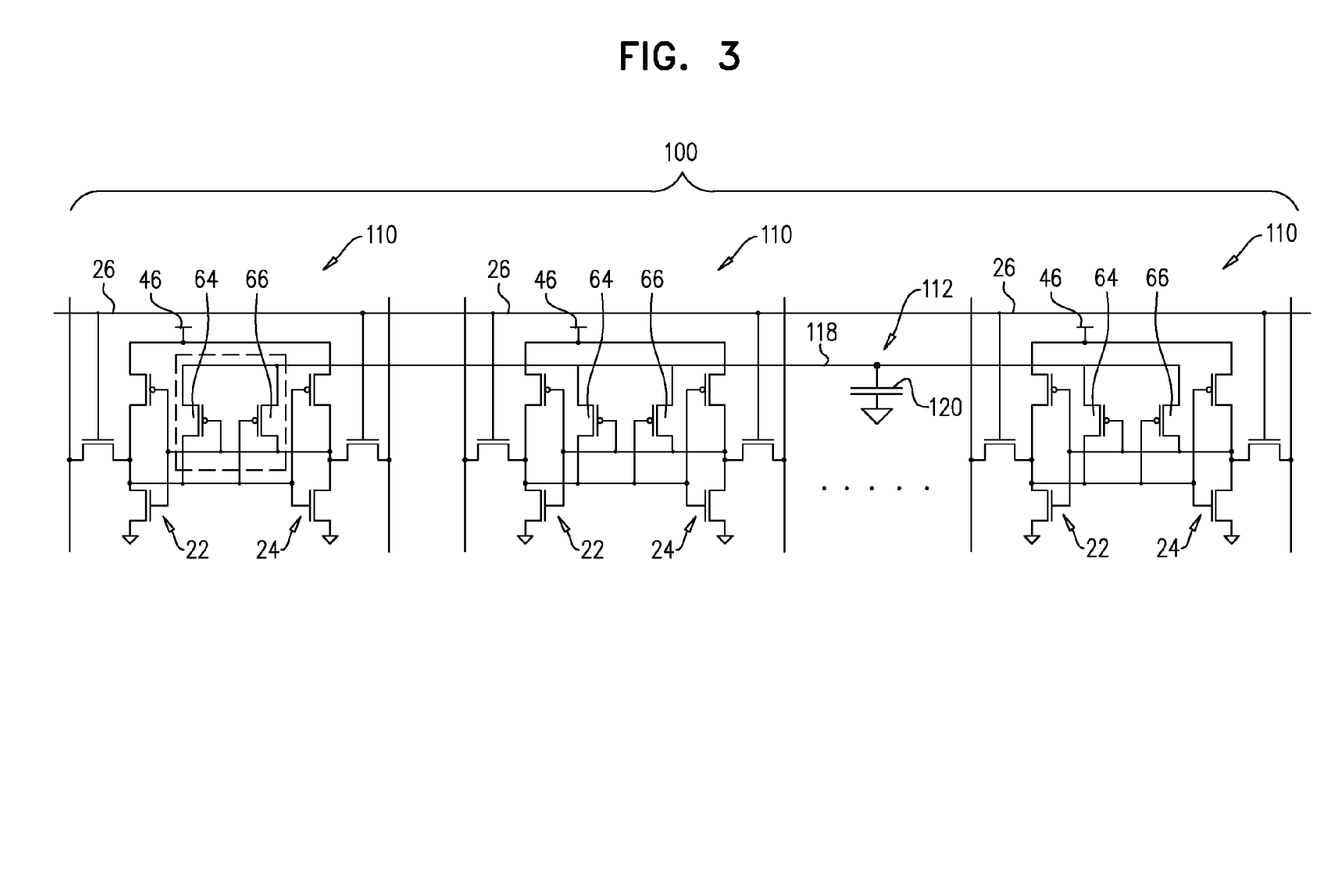
FIG. 3 is a schematic illustration of an assembly comprising a plurality of memory circuits and a common charge reserve, in accordance with some applications of the invention.

Reference is made to FIG. 3, which is a schematic illustration of an assembly 100 comprising a plurality of memory circuits 110 and a common charge reserve 112, in accordance with some applications of the invention. FIG. 3 shows three or more memory circuits 110 purely for illustration, and the scope of the invention includes the option of assembly 100 comprising any number of elements. Except where stated otherwise, each memory circuit 110 is typically identical to memory circuit 60 described hereinabove. For example, each memory circuit comprises (i) cross-coupled inverters 22 and 24 (which together define data-storage portion 30) and (ii) transistors 64 and 66 connected between the inverters. A common connector 118 connects the sources of transistors 64 and 66 of each memory circuit 110 to each other and to the sources of transistors 64 and 66 of the other memory circuits 110.

Capacitance is provided at connector 118, e.g., by an electrical capacitive element (such as a discrete capacitor) 120 coupled to the connector, or by inherent capacitance (such as parasitic capacitance) of the connector (e.g., due to its interaction with surrounding materials, such as the substrate on which the connector is disposed, e.g., a dielectric). Thus, a charge reserve, similar to charge reserve 62, is provided by assembly 100, wherein each memory circuit has its own transistor pair, but common capacitance (e.g., a common electrical capacitive element) is shared among memory circuits.

Figure 4:
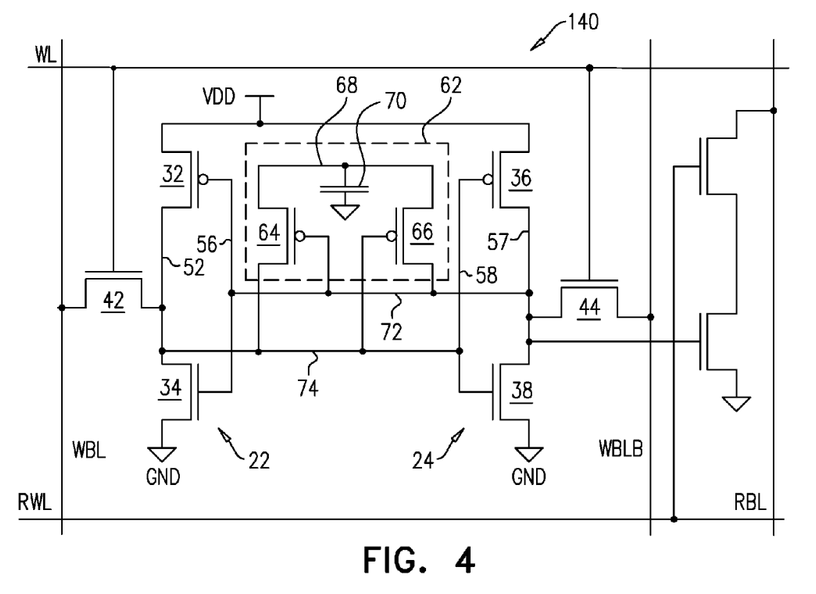
FIGS. 4 and 5 are schematic illustrations of respective memory circuits, each comprising a memory circuit and a charge reserve, in accordance with some applications of the invention.
Figure 5:
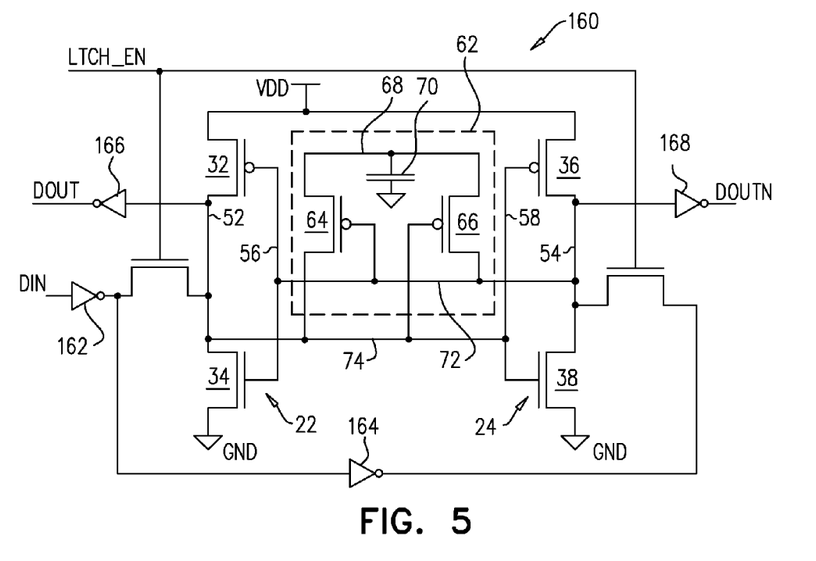

Reference is now made to FIGS. 4 and 5, which are schematic illustrations of a memory circuit 140 and a memory circuit 160 respectively, each comprising memory circuit 20 and charge reserve 62, in accordance with some applications of the invention.

As described with reference to FIG. 2, memory circuit 60 may be described as a 6T SRAM cell that further comprises charge reserve 62. Similarly, memory circuit 140 may be described as an eight-transistor (8T) SRAM cell that further comprises charge reserve 62. 8T SRAM cells have separated write inputs and read output for improved memory stability, especially for operation at very low voltage.

Similarly, memory circuit 160 may be described as a latch circuit that comprises charge reserve 62. This is an example of a level sensitive latch cell, that employs a symmetric, SRAM like, memory circuit, where retention devices are added. Inverters 162 and 164 split the DIN data inputs for writing two complementary data signals to the memory circuit when LTCH_EN is "1". Optional inverters 166 and 168 buffer the data stored inside the memory circuit, to prevent asymmetric load from impacting on the operation of this memory circuit.

Figure 6:
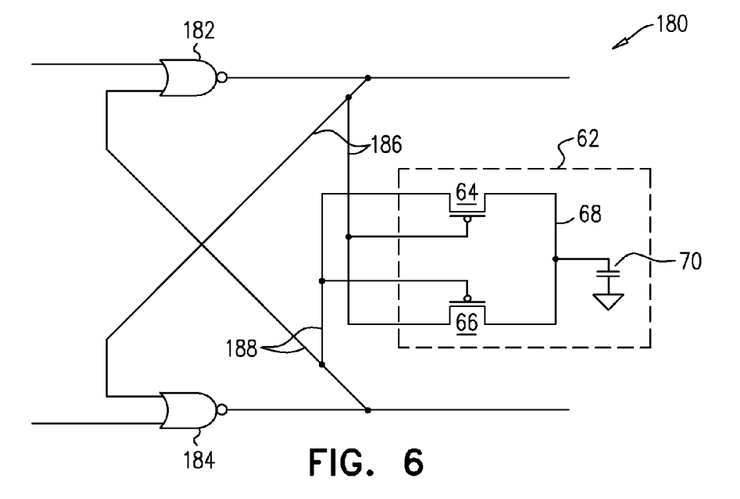
FIG. 6 is a schematic illustration of another memory circuit, in accordance with some applications of the invention.

Reference is made to FIG. 6, which is a schematic illustration of a memory circuit 180, in accordance with some applications of the invention. Memory circuit 180 comprises a set-reset (SR) NOR latch and charge reserve 62. The SR NOR latch comprises two cross-coupled NOR gates (182 and 184), with charge reserve 62 electrically connected therebetween. An electrical connection 186 connects (i) the output of NOR gate 182, (ii) one of the inputs of NOR gate 184, (iii) the gate of transistor 64, and (iv) the drain of transistor 66. Another electrical connection 188 connects (i) the output of NOR gate 184, (ii) one of the inputs of NOR gate 182, (iii) the gate of transistor 66, and (iv) the drain of transistor 64. It is to be understood that the scope of the invention similarly includes an SR NAND latch that comprises charge reserve 62.

Memory circuits 20, 60 and 110 are bistable memory circuits (e.g., symmetrical memory circuits, e.g., memory circuits that comprise cross-coupled inverters). Memory circuits 140, 160 and 180 are described in the present application so as to illustrate that charge reserves such as charge reserve 62 may be used in combination with many bistable memory circuits (e.g., symmetrical memory circuits, e.g., memory circuits that comprise cross-coupled inverters), and are not intended to limit the scope of the invention to the applications shown. Therefore applications of the invention include the use of such charge reserves, mutatis mutandis, in other symmetric SRAM cells (e.g., SRAM cells with any number of transistors), in other SR latches, in NAND latches, in flip-flop circuits based on symmetric, or almost symmetric, memory circuits, and so on.

Figure 7:
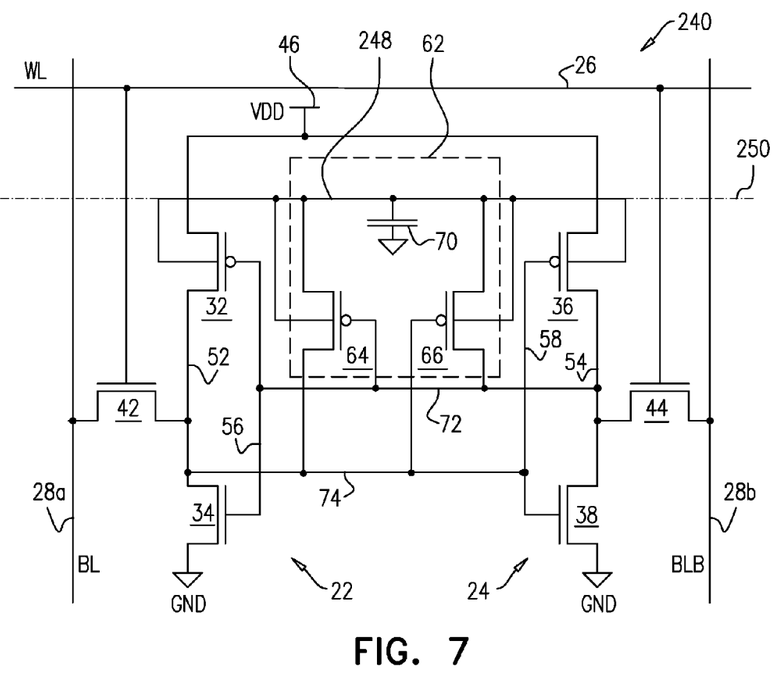
FIG. 7 is a schematic illustration of another memory circuit, in accordance with some applications of the invention.

Reference is made to FIG. 7, which is a schematic illustration of a memory circuit 240, in accordance with some applications of the invention.

For some prior art circuits (e.g., memory circuits), the n-well of each PMOS transistor is in electrical connection with the source of the same transistor. For example, for some applications of prior art memory circuit 20, for each of its PMOS transistors, the n-well may be in electrical connection with the source. For some applications of memory circuit 60, for each of its PMOS transistors, the n-well may be in electrical connection with the source.

Memory circuit 240 is identical to memory circuit 60, except that transistors 32 and 36 are arranged such that the n-well of each of transistors 32 and 36 of the circuit is in electrical connection with the sources (and n-well) of transistors 64 and 66 (e.g., and not in electrical connection with the sources of transistors 32 and 36) of the circuit. For example, a connector 248 (which replaces connector 68 of memory circuit 60) may electrically connect (i) the source of transistor 64, (ii) the source of transistor 66, (iii) the n-well of transistor 32, and (iv) the n-well of transistor 36. The connection to these n-wells provides additional capacitance at connector 248. For some applications this further facilitates not using an additional (or any) discrete capacitor.

For some prior art circuits (e.g., memory circuits), a common n-well is provided for the entire circuit, or for several circuits (such as column of SRAM cells), and the bulk of the each PMOS transistor is in electrical connection with the common n-well. For example, for some applications of prior art memory circuit 20, the source of each of its PMOS transistors may be in electrical connection with a common n-well. For some applications of memory circuit 60, the source of each of its PMOS transistors may be in electrical connection with a common n-well. For some applications, memory circuit 240 has a common n-well. For such applications, memory circuit 240 is identical to applications of memory circuit 60 that utilize a common n-well, except that the respective sources of transistors 32 and 36 are not in electrical connection with the common n-well.

For some applications, a common charge reserve (e.g., as described with reference to FIG. 3, mutatis mutandis) is provided, and the n-wells of the PMOS transistors of multiple memory circuits are electrically connected to the source of the transistors of the common charge reserve (e.g., via an extension 250 of connector 248, shown in phantom in FIG. 7).

This described connection of the n-wells of the PMOS transistors may be used, mutatis mutandis, for other memory circuits described herein, such as memory circuits 60, 110 (or assembly 100), 140, or 160.

It is to be noted that, although memory circuits 60, 140, 160, 180, and 240 are shown as using charge reserve 62, applications of the invention include the use of a common charge reserve (such as common charge reserve 112) with such memory circuits, mutatis mutandis.

Figure 8A:
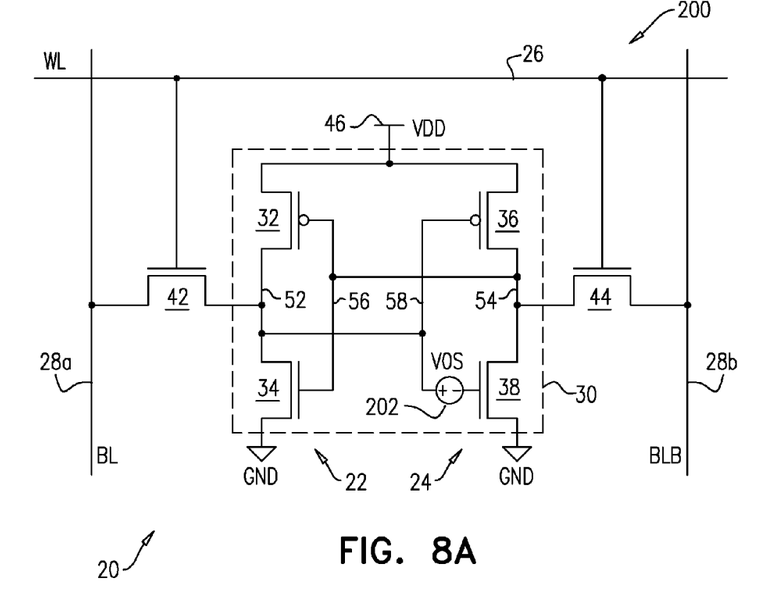
FIGS. 8A-B are schematic illustrations of a circuits used in simulations to test the effect of including a charge reserve in a memory circuit, in accordance with some applications of the invention.
Figure 8B:
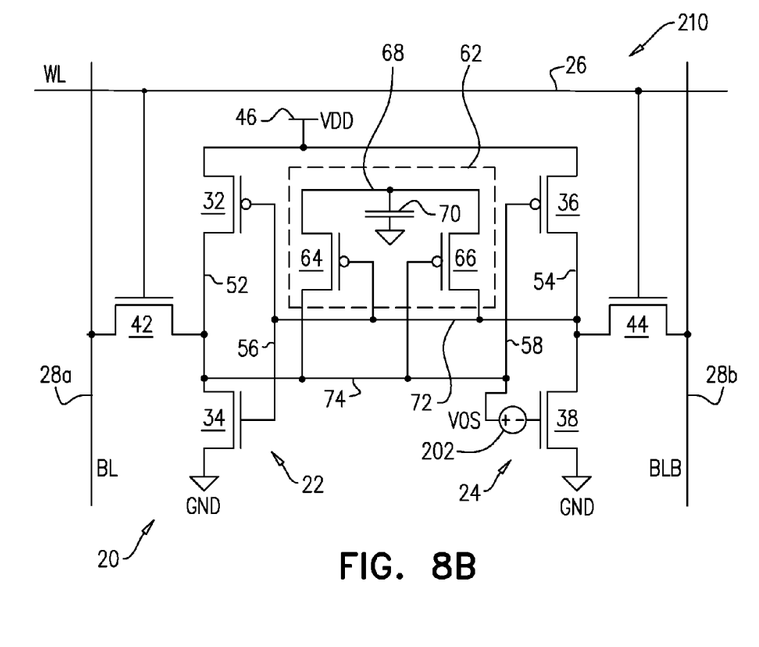
Figure 9:
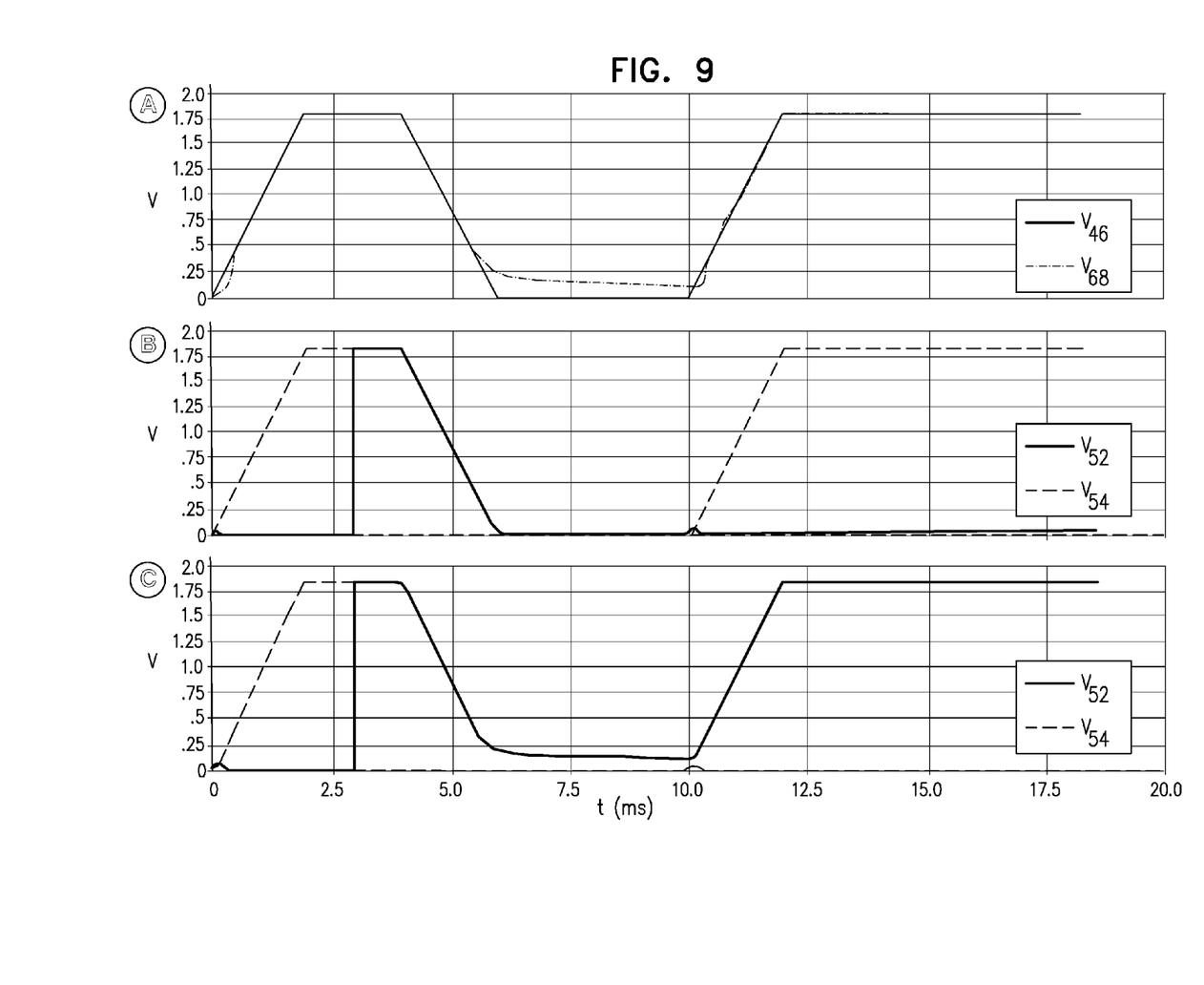
FIG. 9 shows three graphs that represent voltages at various locations of the simulated circuits during the simulations.

Reference is now made to FIGS. 8A-B, and 9. FIGS. 8A-B are schematic illustrations of circuits 200 and 210, respectively, used in simulations to test the effect of including charge reserve 62 in a memory circuit, in accordance with some applications of the invention. Simulated circuits 200 and 210 are identical to memory circuits 20 and 60, respectively, except for the addition of a DC offset voltage (VOS) 202. VOS 202 is used to represent a difference between the threshold voltages of transistors 34 and 38, caused by real-world process variations. For the simulations, VOS was 50 mV, representing maximum mismatch between the thresholds of transistors in advanced CMOS process technologies. Each circuit is biased toward a particular default polarity (i.e., storing a particular default bit). During each simulation, data that is opposite to the default polarity was written. Therefore data loss by these simulated circuits is identifiable by reversion of the circuit to the default bit.

The simulations were performed on 0.18 micron CMOS circuits, operating at 1.8 V nominal voltage. For both simulated circuits, the following procedure was simulated:

Step 1) Over the first 2 ms of the simulation, the VDD voltage was increased from 0 V to 1.8 V. Because of VOS 202, each circuit assumes its default polarity (i.e., stores its default bit).

Step 2) At 3 ms, a bit (the opposite to the default bit of the circuit) is written.

Step 3) At 4 ms, power loss at power supply 46 is simulated, with VDD dropping to 0 V over the following 2 ms.

Step 4) At 10 ms, power return at power supply 46 is simulated, with VDD returning to 1.8 V over the following 2 ms.

Step 5) The bit stored by each circuit (i.e., the polarity of each circuit) is examined, to determine whether data loss occurred.

FIG. 9 shows three graphs (A, B and C) that represent voltages at various locations of the simulated circuits during the simulation. Graph A of FIG. 9 shows (i) the VDD voltage at power supply 46 (solid line) (which is the same for both circuit 200 and circuit 210), and (ii) for simulated circuit 210, the voltage at connector 68 (dashed line). During step 1, as the VDD voltage approaches 0.2-0.3 V, the voltage at connector 68 begins to increase, and then matches the VDD voltage. Both voltages drop during step 3. However, although the VDD voltage at power supply 46 drops to 0 V within 2 ms (by t=6 ms), the voltage drop at connector 68 begins to slow down at about 0.4 V, and the voltage at connector 68 does not reach zero by the time that power restoration occurs at t=10 ms.

Graphs B and C show, for simulated circuits 200 and 210 respectively, the voltage at input 52 (solid line), and the voltage at input 54 (dashed line). During step 1, as the VDD voltage at power supply 46 increases (as shown in graph A), for both circuits the voltage at input 54 increases correspondingly, while the voltage at input 52 remains at zero. At t=2 ms (and until t=3 ms) the polarity of both circuits may therefore be described as 52=GND:54=VDD—which according to the convention of this patent application, represents a stored 0. At step 2, the bit is written by applying a write-enable pulse (not visible in the graphs) via word line 26, which reverses the polarity of both circuits to 52=VDD:54=GND—which according to the convention of this patent application, represents a stored 1. That is, the voltage at input 52 is high (1.8 V) and the voltage at input 54 is low (0 V).

During step 3, as the VDD voltage at power supply 46 drops (shown in graph A), the voltage at input 52 correspondingly drops. In simulated circuit 200, the voltage at input 52 reaches zero by about t=6 ms, which is about the same time that the VDD voltage at power supply 46 reaches zero. However, in simulated circuit 210, by t=10 ms the voltage at input 52 has not yet reached zero.

During step 4, as the VDD voltage at power supply 46 returns to 1.8 V, the effect of the inclusion of charge reserve 62 becomes apparent: Circuit 200 reverts to its default polarity of 52=GND:54=VDD (stored 0). In contrast, for circuit 210, because the voltage at connector 68 (and at input 52) remained sufficiently above zero until power was restored to the circuit, circuit 210 remains at 52=VDD:54=GND (stored 1). That is, simulated circuit 200 suffered from data loss during the brief power interruption, whereas simulated circuit 210 retained its stored data bit during the power interruption.

Reference is made to FIGS. 1-9. Although charge reserve 62 is shown as comprising two PMOS transistors, it is to be noted that for some applications two NMOS transistors are used to provide a charge reserve, mutatis mutandis.

Reference is again made to FIGS. 1-9. It is noted that the memory circuits (e.g., memory elements) described herein may be useful for applications in which volatile memory is expected to experience power interruptions (e.g., brief power interruptions). For some applications, the memory circuits described herein may be used as components in a medical implant, such as a wirelessly-powered and battery-less medical implant. For example, the memory circuits described herein may be used as components in an artificial retina implant, e.g., an optically-powered (e.g., infra-red-powered and/or laser-powered) artificial retina implant, such as described in one or more of the following references, which are incorporated herein by reference:

U.S. Pat. No. 8,150,526; PCT Application Publication WO/2010/089739; US Patent Application Publication 2012/0041514; US Patent Application Publication 2014/0188222; U.S. Pat. No. 8,718,748; PCT Application Publication WO/2011/086545; U.S. Pat. No. 8,428,740; PCT Application Publication WO/2012/017426; U.S. Pat. No. 8,442,641; PCT Application Publication WO/2012/153325; U.S. Pat. No. 8,571,669; PCT Application Publication WO/2012/114327; US Patent Application Publication 2014/0143559; PCT Application Publication WO/2014/080343; US Patent Application Publication 2014/0277435; US Patent Application Publication 2015/0207572; US Patent Application Publication 2015/0182748; and in particular, U.S. Pat. No. 8,706,243 to Gefen et al.

Figure 10:
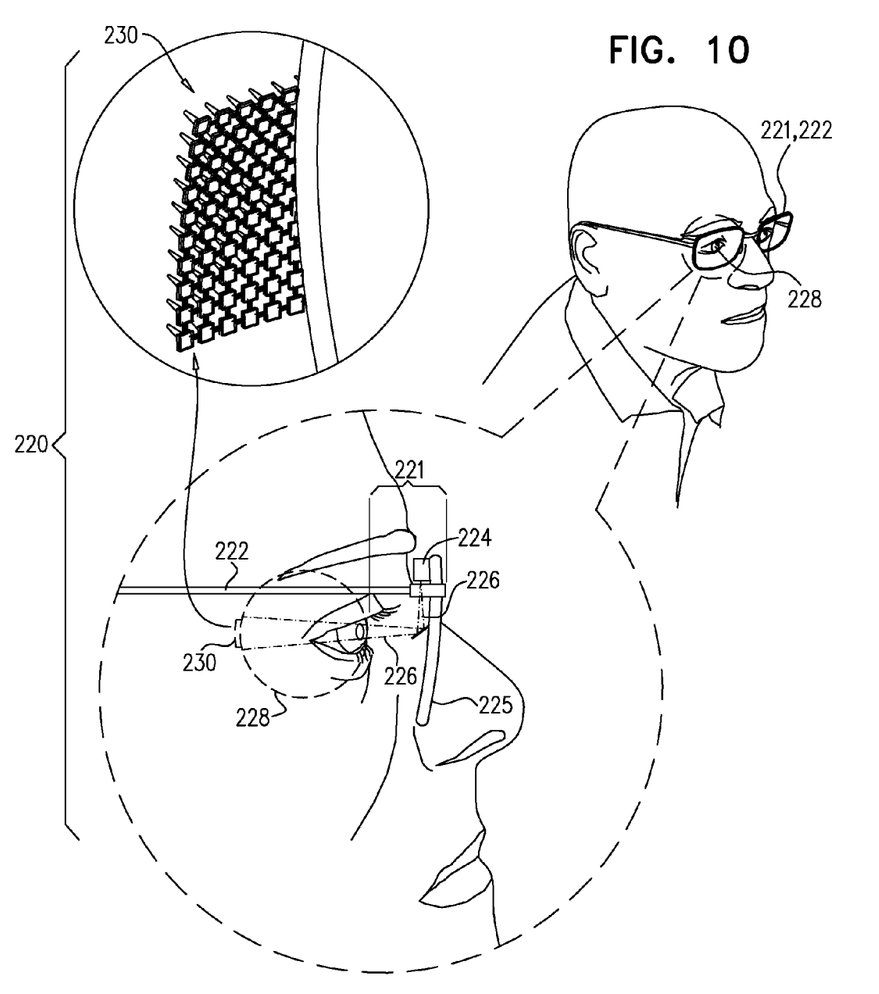
FIG. 10 is a schematic illustration of apparatus comprising an optically-powered artificial retina implant that comprises a memory circuit, in accordance with some applications of the invention.

Reference is made to FIG. 10, which is a schematic illustration of apparatus 220 comprising an optically-powered artificial retina implant that comprises a memory circuit, in accordance with some applications of the invention. Apparatus 220 comprises an external device 221 comprising a mount 222, which is typically a pair of eyeglasses, and is placed in front of a subject's eye 228. External device 221 further comprises an optical power source, for example a laser 224, which is coupled to the mount and is configured to emit radiated energy 226 that is outside the visible range toward the subject's eye 228. Laser 224 is shown coupled to the inner part of an eyeglass lens 225 by way of illustration and not limitation. Laser 224 may be coupled to other members of mount 222 for example, to the arm of the eyeglasses.

Apparatus 220 additionally comprises an intraocular device (i.e., an intraocular implant) 230, which is implanted entirely in eye 228. Intraocular device 230 comprises a small (e.g., 3-6 mm in diameter), thin (e.g., less than 2 mm thick) micro-electrode array. Intraocular device 230, in accordance with embodiments of the present invention, is typically configured to be implanted in the epi-retinal space of eye 228. In either location, intraocular device 230 receives visible light that emanates from objects and enters the eye. The visible light strikes photosensors of the intraocular device, which generate a signal via intermediate circuitry causing electrodes on the intraocular device to stimulate retinal sensory neurons (for example bipolar cells), resulting in the sensation of an image. Stimulation of the bipolar cells activates and utilizes the intact optics and processing mechanisms of the eye.

Intraocular device 230 comprises circuitry configured to, in response to light striking the photoreceptors of the intraocular device, process the resulting photocurrent and drive the electrodes of the intraocular device. This circuitry comprises a volatile memory device that includes one or more memory circuits (such as a memory circuit described herein), in which data such as configuration or calibration settings are stored. The volatile memory device comprises one or more charge reserves described herein (e.g., each memory circuit comprises a charge reserve 62, or common charge reserve(s) 112 are shared by several memory circuits), which are charged during normal functioning of the memory circuits, and preserve the data stored in the memory circuits during brief interruptions of the power supplied by external device 221 to intraocular device 230 that may be caused, for example, by blinking or saccade of the eye.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a volatile memory device comprising one or more memory circuits, each memory circuit comprising:
a first CMOS inverter, having a first input and a first output;
a second CMOS inverter, cross-coupled to the first CMOS inverter, and having a second input and a second output;
a first PMOS transistor, having a first source, a first gate, and a first drain;
a second PMOS transistor, having a second source electrically connected to the first source, a second gate, and a second drain;
a first connector, electrically connecting:
the first output,
the first drain,
the second gate, and
the second input; and
a second connector, electrically connecting:
the second output,
the second drain,
the first gate, and
the first input,
wherein:
the first PMOS transistor has a first-transistor threshold voltage,
the first CMOS inverter comprises a third PMOS transistor having a third-transistor threshold voltage, and
the first PMOS transistor is configured such that the first-transistor threshold voltage is greater than the third-transistor threshold voltage.

2. The apparatus according to claim 1, wherein:
the third PMOS transistor has a third source, a third gate, a third drain, and a third-transistor n-well,
the second CMOS inverter comprises a fourth PMOS transistor having a fourth source, a fourth gate, a fourth drain, and a fourth-transistor n-well, and
each memory circuit further comprises a third connector, electrically connecting the first source, the second source, the third-transistor n-well, and the fourth-transistor n-well.

3. The apparatus according to claim 1, wherein each memory circuit is an SRAM cell.

4. The apparatus according to claim 1, wherein each memory circuit is a latch.

5. The apparatus according to claim 1, wherein each memory circuit further comprises a third connector, electrically connecting the first source and the second source, wherein each memory circuit further comprises an electrical capacitive element that comprises a first conductor and a second conductor, and wherein the third connector electrically connects the first source, the second source, and the first conductor.

6. The apparatus according to claim 5, wherein the electrical capacitive element comprises a distinct capacitor.

7. The apparatus according to claim 1, wherein each memory circuit further comprises a third connector, electrically connecting the first source and the second source, and wherein the apparatus further comprises a dielectric in electrical contact with the third connector.

8. The apparatus according to claim 7, wherein the dielectric is a substrate on which the first, second, and third connectors are disposed.

9. The apparatus according to claim 1, wherein the one or more memory circuits comprises at least a first memory circuit and a second memory circuit, and wherein the apparatus further comprises a third connector, electrically connecting:
the first source of the first memory circuit,
the second source of the first memory circuit,
the first source of the second memory circuit, and
the second source of the second memory circuit.

10. The apparatus according to claim 9, further comprising an electrical capacitive element that comprises a first conductor and a second conductor, wherein the third connector electrically connects:
the first conductor,
the first source of the first memory circuit,
the second source of the first memory circuit,
the first source of the second memory circuit, and
the second source of the second memory circuit.

11. The apparatus according to claim 10, wherein the electrical capacitive element comprises a distinct capacitor.

12. The apparatus according to claim 9, further comprising a dielectric in electrical contact with the third connector.

13. The apparatus according to claim 12, wherein the dielectric is a substrate on which the first, second, and third connectors are disposed.

14. The apparatus according to claim 1, wherein the apparatus comprises a medical implant that comprises the device.

15. The apparatus according to claim 14, wherein the medical implant is an artificial retina implant.

16. The apparatus according to claim 1, wherein each memory circuit is a six-transistor SRAM cell.

17. The apparatus according to claim 1, wherein each memory circuit is an eight-transistor SRAM cell.

18. The apparatus according to claim 1, wherein each memory circuit is a ten-transistor SRAM cell.

19. The apparatus according to claim 1, wherein the first PMOS transistor is configured such that the first-transistor threshold voltage is greater than the third-transistor threshold voltage by between 0.05 and 0.2 V.

20. A Static Random Access Memory (SRAM) device, comprising one or more SRAM cells, each SRAM cell comprising:
   a first CMOS inverter, having a first input and a first output;
   a second CMOS inverter, cross-coupled to the first CMOS inverter, and having a second input and a second output;
   a first PMOS transistor, having a first source, a first gate, and a first drain;
   a second PMOS transistor, having a second source, a second gate, and a second drain;
   an electrical capacitive element, comprising a first conductor and a second conductor;
   a first connector, electrically connecting:
      the first output,
      the first drain,
      the second gate, and
      the second input;
   a second connector, electrically connecting:
      the second output,
      the second drain,
      the first gate, and
      the first input; and
   a third connector, electrically connecting:
      the first source,
      the second source, and
      the first conductor.

21. Apparatus comprising a volatile memory device comprising one or more memory circuits, each memory circuit comprising:
   a first CMOS inverter, having a first input and a first output;
   a second CMOS inverter, cross-coupled to the first CMOS inverter, and having a second input and a second output;
   a first PMOS transistor, having a first source, a first gate, and a first drain;
   a second PMOS transistor, having a second source electrically connected to the first source, a second gate, and a second drain;
   a first connector, electrically connecting:
      the first output,
      the first drain,
      the second gate, and
      the second input; and
   a second connector, electrically connecting:
      the second output,
      the second drain,
      the first gate, and
      the first input,
wherein each memory circuit further comprises a third connector, electrically connecting the first source and the second source, wherein each memory circuit further comprises an electrical capacitive element that comprises a first conductor and a second conductor, and wherein the third connector electrically connects the first source, the second source, and the first conductor.

22. The apparatus according to claim 21, wherein the electrical capacitive element comprises a distinct capacitor.

23. The apparatus according to claim 18, wherein:
   the first PMOS transistor has a first-transistor threshold voltage,
   the first CMOS inverter comprises a third PMOS transistor having a third-transistor threshold voltage, and
   the first PMOS transistor is configured such that the first-transistor threshold voltage is greater than the third-transistor threshold voltage.

24. Apparatus comprising a volatile memory device comprising one or more memory circuits, each memory circuit comprising:
   a first CMOS inverter, having a first input and a first output;
   a second CMOS inverter, cross-coupled to the first CMOS inverter, and having a second input and a second output;
   a first PMOS transistor, having a first source, a first gate, and a first drain;
   a second PMOS transistor, having a second source electrically connected to the first source, a second gate, and a second drain;
   a first connector, electrically connecting:
      the first output,
      the first drain,
      the second gate, and
      the second input; and
   a second connector, electrically connecting:
      the second output,
      the second drain,
      the first gate, and
      the first input,
wherein each memory circuit further comprises a third connector, electrically connecting the first source and the second source, and wherein the apparatus further comprises a dielectric in electrical contact with the third connector.

25. The apparatus according to claim 24, wherein the dielectric is a substrate on which the first, second, and third connectors are disposed.

26. Apparatus comprising a volatile memory device comprising one or more memory circuits, each memory circuit comprising:
   a first CMOS inverter, having a first input and a first output;
   a second CMOS inverter, cross-coupled to the first CMOS inverter, and having a second input and a second output;
   a first PMOS transistor, having a first source, a first gate, and a first drain;
   a second PMOS transistor, having a second source electrically connected to the first source, a second gate, and a second drain;
   a first connector, electrically connecting:
      the first output,
      the first drain,
      the second gate, and
      the second input; and
   a second connector, electrically connecting:
      the second output,
      the second drain,
      the first gate, and
      the first input,
wherein:

the one or more memory circuits comprises at least a first memory circuit and a second memory circuit, the apparatus further comprises a third connector, electrically connecting:
- the first source of the first memory circuit,
- the second source of the first memory circuit,
- the first source of the second memory circuit, and
- the second source of the second memory circuit, the apparatus further comprises an electrical capacitive element that comprises a distinct capacitor that comprises a first conductor and a second conductor, the third connector electrically connects:
- the first conductor,
- the first source of the first memory circuit,
- the second source of the first memory circuit,
- the first source of the second memory circuit, and
- the second source of the second memory circuit, and the electrical capacitive element comprises a distinct capacitor.

27. Apparatus comprising a volatile memory device comprising one or more memory circuits, each memory circuit comprising:

a first CMOS inverter, having a first input and a first output;

a second CMOS inverter, cross-coupled to the first CMOS inverter, and having a second input and a second output;

a first PMOS transistor, having a first source, a first gate, and a first drain;

a second PMOS transistor, having a second source electrically connected to the first source, a second gate, and a second drain;

a first connector, electrically connecting:
- the first output,
- the first drain,
- the second gate, and
- the second input; and a second connector, electrically connecting:
- the second output,
- the second drain,
- the first gate, and
- the first input, wherein:

the one or more memory circuits comprises at least a first memory circuit and a second memory circuit, and wherein the apparatus further comprises a third connector, electrically connecting:
- the first source of the first memory circuit,
- the second source of the first memory circuit,
- the first source of the second memory circuit, and
- the second source of the second memory circuit, and the apparatus further comprises a dielectric in electrical contact with the third connector.

* * * * *